(12) United States Patent
Quarry et al.

(10) Patent No.: US 7,195,395 B2
(45) Date of Patent: Mar. 27, 2007

(54) DENTAL SENSOR CLAMP

(75) Inventors: Antony Quarry, Caslano (CH); Beat Kilcher, Bosco Luganese (CH); Marco Da Rold, Odogno (CH); Rolf M. Klauser, Kriens (CH)

(73) Assignee: KerrHawe SA, Bioggio (CH)

( * ) Notice: Subject to any disclaimer, the term of this patent is extended or adjusted under 35 U.S.C. 154(b) by 7 days.

(21) Appl. No.: 11/068,123

(22) Filed: Feb. 28, 2005

(65) Prior Publication Data

US 2006/0193442 A1     Aug. 31, 2006

(51) Int. Cl.
  *A61B 6/14*  (2006.01)
  *G03B 42/04* (2006.01)
(52) U.S. Cl. ............................ 378/170; 378/191
(58) Field of Classification Search ............. 378/191, 378/170; D24/161
   See application file for complete search history.

(56) References Cited

U.S. PATENT DOCUMENTS

| | | | |
|---|---|---|---|
| 1,576,477 A | | 3/1926 | Wiens |
| 2,090,933 A | * | 8/1937 | Bolin ............... 378/170 |
| 2,245,395 A | * | 6/1941 | Goldberg ............. 378/170 |
| 2,688,096 A | | 8/1954 | Galliano et al. |
| 2,753,461 A | * | 7/1956 | Goldberg ............. 378/170 |
| 3,771,781 A | | 11/1973 | Lackey et al. |
| 4,057,732 A | | 11/1977 | Klauser |
| 4,707,847 A | * | 11/1987 | Van Aken ............. 378/170 |
| 4,965,885 A | * | 10/1990 | Fuhrmann ............. 378/168 |
| 5,090,047 A | * | 2/1992 | Angotti et al. ........ 378/170 |
| 5,317,619 A | | 5/1994 | Hellmick et al. |
| 5,799,058 A | | 8/1998 | Willis et al. |
| 6,203,195 B1 | | 3/2001 | Willis |
| 6,276,827 B1 | | 8/2001 | Nakamura et al. |
| 6,343,875 B1 | | 2/2002 | Eppinger et al. |
| 6,540,399 B1 | * | 4/2003 | Eppinger et al. ........ 378/170 |
| 6,905,244 B2 | * | 6/2005 | Kilcher et al. ......... 378/170 |
| 2004/0096040 A1 | | 5/2004 | Kilcher et al. |

FOREIGN PATENT DOCUMENTS

CA    2 324 871    4/2002
FR    1 088 070    3/1955

OTHER PUBLICATIONS

European Patent Office, Communication and European Search Report, Application No. 06250003.8, dated Jun. 23, 2006 (5 pages).

\* cited by examiner

*Primary Examiner*—Edward J. Glick
*Assistant Examiner*—Thomas R. Artman
(74) *Attorney, Agent, or Firm*—Wood, Herron & Evans, L.L.P.

(57) ABSTRACT

A dental sensor clamp has a clamp body with a connector on one end for connecting the sensor clamp to a bite plate. A clamp body opposite end has a fixed stop locatable adjacent an apical area of a tooth. A clamping slide is mounted within a thickness of the clamp body, and the clamping slide supports a member providing a resilient clamping force upon the member being moved against the sensor and the fixed stop. The dental sensor clamp reliably secures an imaging sensor adjacent the apical area of the tooth.

20 Claims, 8 Drawing Sheets

DENTAL SENSOR CLAMP

FIELD OF THE INVENTION

The present invention relates generally to dentistry and, more particularly, to a dental clamp for a sensor.

BACKGROUND OF THE INVENTION

It is known to generate images of a patient's teeth in order to determine their state of health as well as to diagnose and treat diseases. Further, for the treatment of diseases or injuries that affect the root tip or nerve of the tooth, an image or other presentation of the periapical area of the teeth is most desirable. As used herein, "an image or other presentation of the periapical area of the teeth" means an image or other presentation that shows the whole tooth both above and below the gum line. Such images and presentations include radiographs recorded on X-ray film and images provided by a digital image sensor.

Digital images are captured by either digital imaging plates located within the patient's mouth or a digital imaging sensor that provides a signal via a cable or wireless transmission to a computer that generates a visual display of the periapical area of the teeth. Generally, X-ray films and imaging plates are of standard sizes and therefore, are subject to being supported by a holder of a fixed size, which can be accommodated in the patient's mouth with reasonable comfort. In contrast, digital sensors do not have standard dimensions and are often relatively large and bulky and are often connected to an electrical cable; and thus, the handling of digital sensors in the patient's mouth is somewhat problematic and often uncomfortable for the patient. As used herein "mouth" means an oral cavity containing the tongue and teeth between the lips and the pharynx.

Imaging mediums including digital sensors are commercially available in different sizes that produce different image formats. It is known to provide different size holders to accommodate different size imaging mediums and digital sensors. There are also known holders that can accommodate digital imaging sensors of different sizes; however, commercially available holders have several disadvantages.

Commercially available holders locate and clamp a sensor with respect to a locating surface adjacent to a bite plate that is clenched between the patient's teeth. By locating and securing the sensor adjacent to the bite plate, the apical area of the tooth is often outside the field of vision of the sensor and thus, not included in the image. As used herein, the "apical area" refers to the portion of the tooth around the root area of the tooth. The absence of apical area in the image requires further imaging by reorienting the sensor or using a larger sensor. In either event, valuable time in the dental suite is lost with a further penalty of additional patient discomfort and irritation. Therefore, there is a need for a sensor holder that accurately, reliably and repeatedly locates and secures sensors of different sizes in the oral cavity, so that the apical area is included in the image or presentation and a complete presentation of the periapical area of the teeth is obtained.

Sensor clamps have either a passive structure that have no moving parts and clamping is accomplished by opposed resilient clamp arms or, an active structure in which a clamping action is obtained by one or more parts being movable with respect to other parts. With such active structures, a movable part is often layered on a static part or a movable part is partially or wholly enclosed by a static part. In either event, the sensor clamp has a bulk and thickness that is often greater than sensor clamps of a passive structure. Further, portions of the sensor clamp often overlay an imaging field of the sensor, and those sensor clamp portions can appear as artifacts or shadows in the resulting image. Further, with active structures, additional artifacts or shadows can be caused by movable parts of active structures that present different thicknesses in the imaging field. Therefore, there is a need for a sensor holder of an active structure that substantially reduces and minimizes artifacts and shadows in a resulting image.

Known sensor holders often have a movable part partially or wholly enclosed within a static part, thereby forming enclosed volumes within the sensor clamp structure. Such enclosed volumes present barriers to the flow of steam or other sterilizing fluid and are difficult to completely sterilize between uses. Therefore, there is a need for a sensor clamp having an active structure that can be easily and reliably sterilized between uses.

Commercially available sensor holders capture the sensor between movable arms or pads that can be locked in place. However, if the sensor is not carefully located and tightly secured between the arms, the sensor may experience motion, which often adversely affects the quality of the presentation of the resultant image. Therefore, there is a need for a sensor holder in which the sensor is more securely mounted and secured.

SUMMARY OF THE INVENTION

The present invention provides dental sensor clamps that locate and secure sensors of different sizes such that full and high quality images of the periapical area of the anterior and posterior teeth are provided. The dental sensor clamps of the present invention are easy to use and provide consistent positioning of the sensors near the apical area of the teeth. The dental sensor clamps of the present invention provide high quality images with a minimum of artifacts and shadows, can be reliably sterilized between uses, are more comfortable for patients and are especially useful in endodontics.

According to the principles of the present invention and in accordance with the described embodiments, the invention provides a dental sensor clamp for holding a sensor in a mouth of a patient, which is used to provide images of a patient's teeth. The dental sensor clamp has a clamp body with a connector on one end for connecting the sensor clamp to a bite plate. An opposite end of the clamp body has a fixed stop locatable adjacent an apical area of a tooth. A member is mounted on, and movable with respect to, the clamp body. The member has structure for providing a resilient clamping force against the sensor as the member is moved toward from the fixed stop, thereby securing the sensor against the fixed stop. Thus, the sensor is located and secured adjacent the apical area of the tooth.

In an alternative embodiment, the dental sensor clamp body has a first portion at the one end connectable to a bite plate and a second portion between the ends of the clamp body. The clamp slide is located within a thickness of the second portion, thereby providing a relatively thin clamp body, which facilitates obtaining optimal images from the sensor.

In a further embodiment, the clamp body has a slot extending longitudinally in the clamp body. Tabs extend from opposite walls of the slot, and the clamp slide is located in the slot and between the tabs to be movable toward and away from the fixed stop. This open structure, with no cover plate over the clamp slide, permits reliable sterilization between uses.

These and other objects and advantages of the present invention will become more readily apparent during the following detailed description taken in conjunction with the drawings herein.

BRIEF DESCRIPTION OF THE DRAWINGS

The accompanying drawings, which are incorporated herein and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1A:
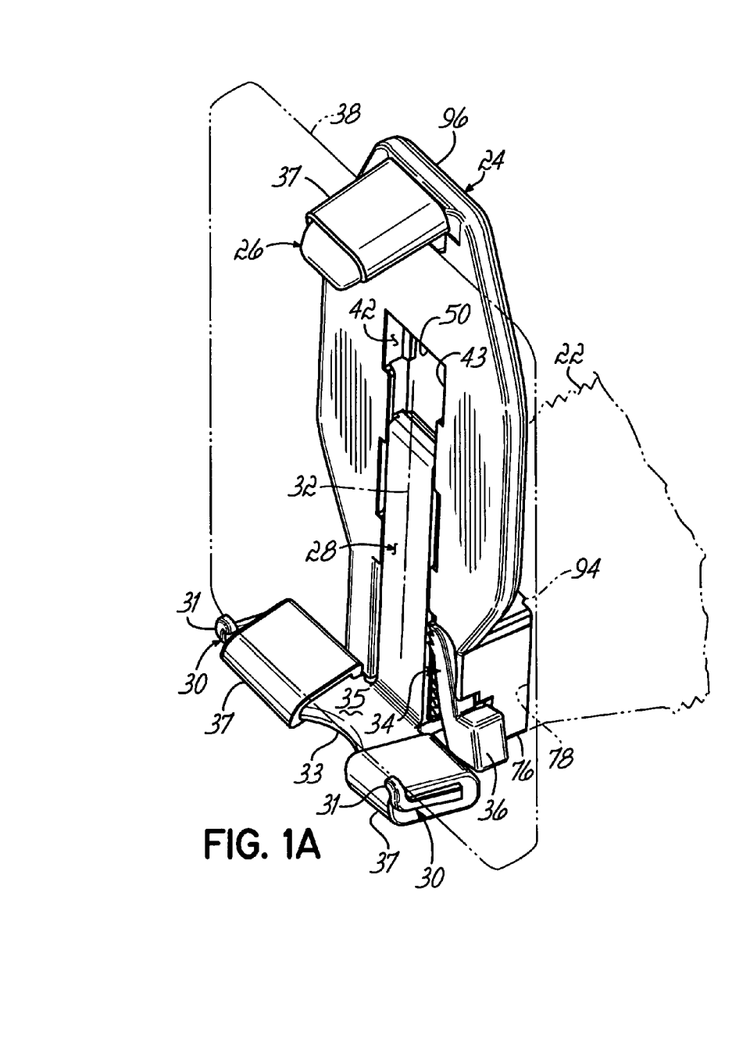
FIGS. 1A and 1B are respective rear and front perspective views of an anterior clamp used to hold a device for imaging anterior teeth in accordance with the principles of the present invention.
Figure 1B:
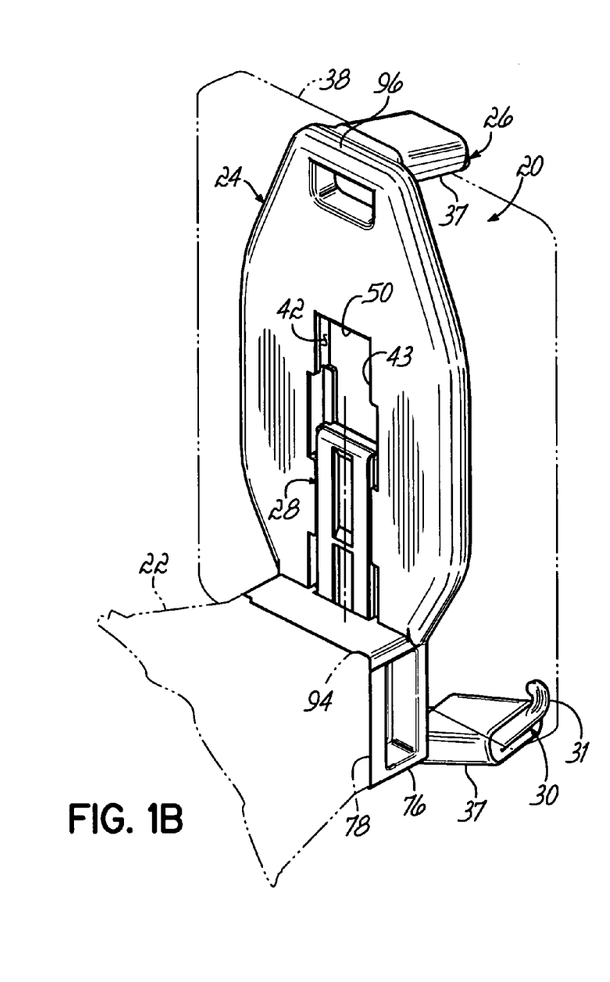

Referring to FIGS. 1A and 1B, an anterior sensor clamp 20 is attachable to an anterior bite plate 22 shown in phantom. The anterior sensor clamp 20 has an anterior clamp body 24 with an upper fixed stop 26. A clamp slide 28 is mounted for sliding movement in the clamp body 24, and the clamp slide 28 has a pair of resilient clamping arms 30 that extend in opposite directions from a clamp slide centerline 32. The fixed stop 26 and resilient arms 30 are covered by a soft, compliant material 37, for example, rubber pads, which are compatible with, and do not damage, a hygienic pouch or other protective envelope that is placed over the sensor during use.

To open the sensor clamp 20, a pivotable anterior release arm 34 is moved out of locking engagement with the clamp slide 28 by pushing a release button 36 formed on an outer end of the release arm 34. With the release button 36 depressed, the clamp slide 28 is movable or slidable with respect to the clamp body 24 in a generally longitudinal direction away from the fixed stop 26.

To load a sensor 38, (shown in phantom), for example, a wired or wireless digital sensor, a user places the sensor 38 between the fixed stop 26 and the resilient arms 30. By simply pushing on a lower surface 33 of the clamp slide 28 at the clamp slide centerline 32, the flexible arms 30 and sensor 38 are secured against the fixed stop 26. Continued pressure causes the resilient arms 30 to flex and apply a resilient clamping force against the sensor 38 and fixed stop 26. The release arm 34 automatically locks the clamp slide 28 in place upon the user releasing the clamp slide 28. The sensor 38 is released from the sensor clamp 20 by simply pushing the release button 36, which unlocks the clamping slide 28. The resilient arms 30 are then free to return to their unflexed state, which causes the clamping slide 28 to quickly move away from the sensor 38; and the sensor clamp 20 "snaps" open.

Figure 2A:
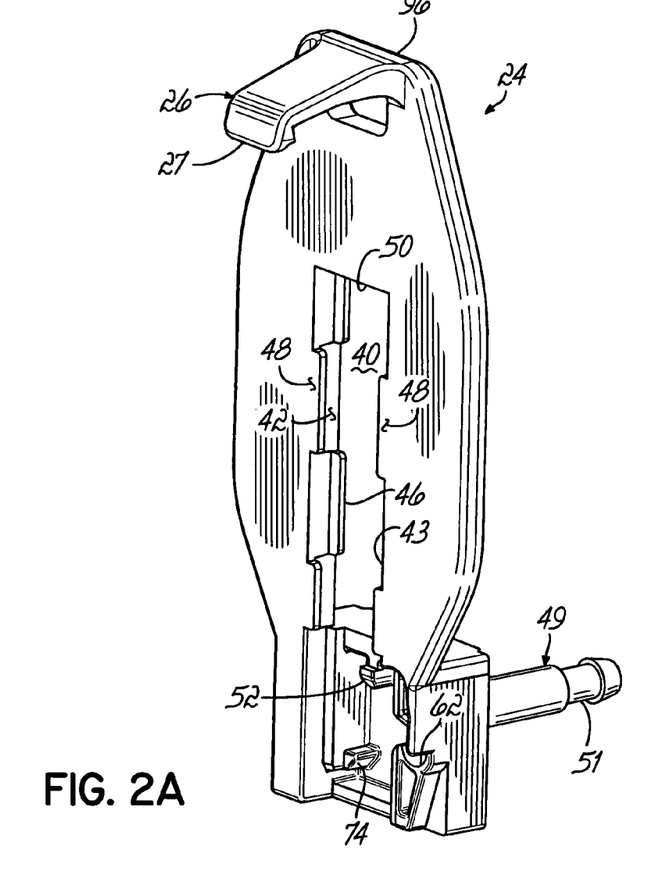
FIGS. 2A and 2B are respective rear and front perspective views of a clamp body used with the anterior sensor clamp of FIGS. 1A and 1B.
Figure 2B:
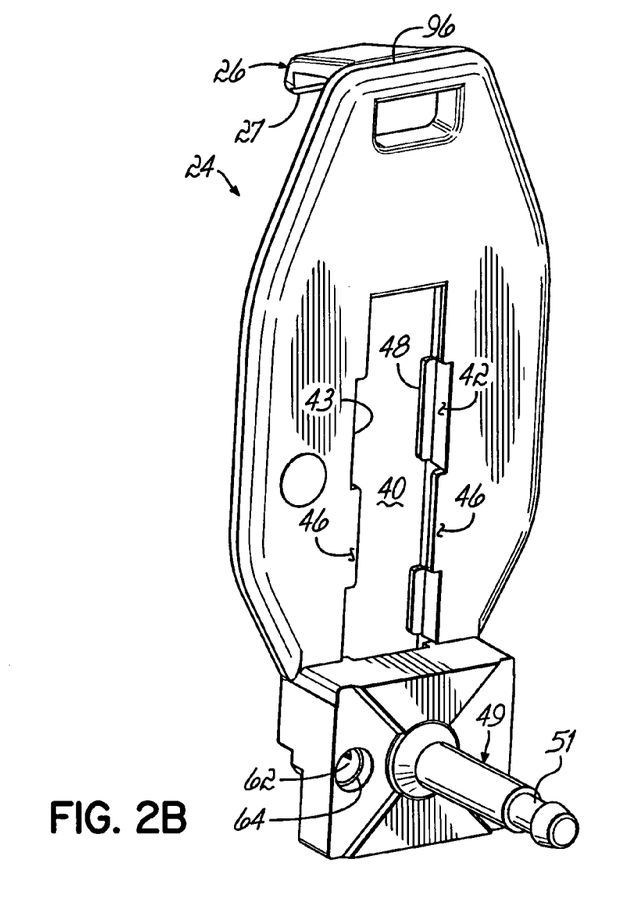

Referring to FIGS. 2A and 2B, the anterior clamp body 24 of the anterior sensor clamp 20 has a centrally located opening or slot 40 with opposed sidewalls 42, 43. The clamp slide 28 shown in detail in FIG. 3 has a longitudinally extending projection or guide rail 44 on one side and a longitudinally extending toothed rack 45. The clamp slide 28 is located between the sidewalls 42, 43 of the clamp body 24 as shown in FIGS. 1A and 1B. The guide rail 44 and rack 45 have a thickness less than a thickness of the center portion of the clamp slide 28, and the guide rail 44 and rack 45 are captured between pairs of opposed front tabs 46 and pairs of opposed rear tabs 48. The front tabs 46 are separated from the rear tabs 48 by a thickness of the sidewalls 42, 43, which is slightly more than a thickness of the guide rail 44 and rack 45. With the anterior clamp body 24, travel of the clamp slide 28 toward the fixed stop 26 is limited by an upper edge or wall 50 of the slot 40. Motion of the clamp slide 28 in an opposite direction away from the fixed stop 26 is limited by a slide stop 52 shown in FIG. 2A.

Figures 3, 4:
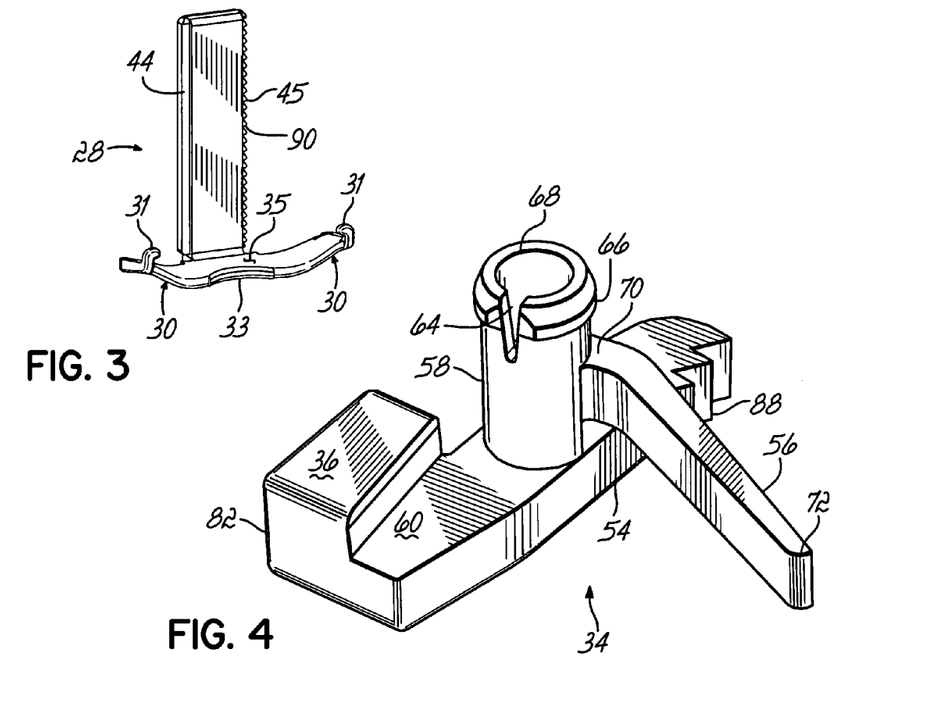
FIG. 3 is a perspective view of a clamp slide used with the anterior sensor clamp of FIGS. 1A and 1B.
FIG. 4 is a perspective view of a release arm used with the anterior sensor clamp of FIGS. 1A and 1B.
Figure 5:
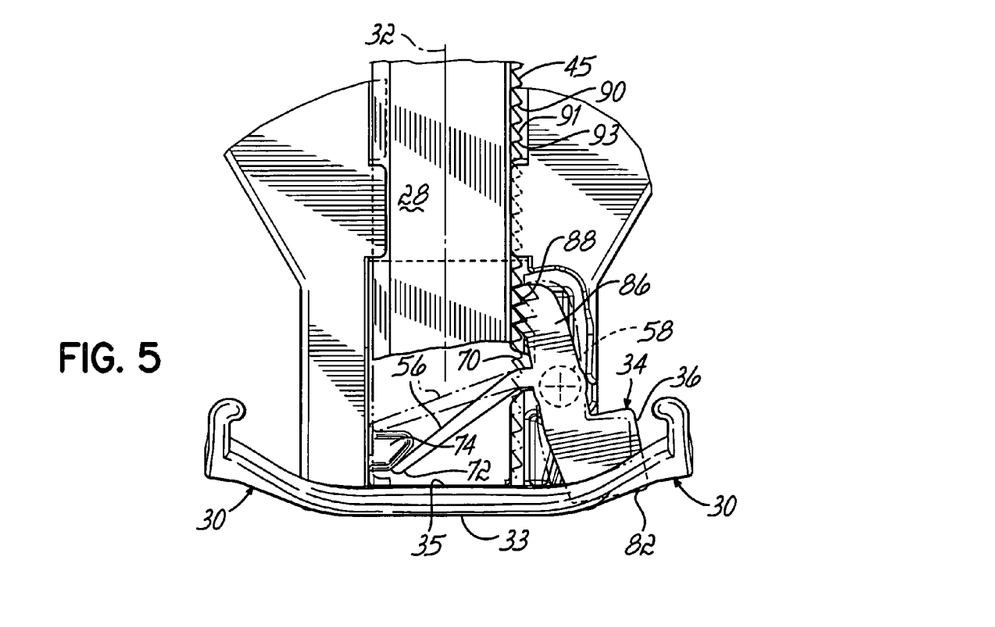
FIG. 5 is a partial rear elevation view of the anterior sensor clamp of FIGS. 1A and 1B.

Referring to FIG. 4, the release arm 34 for the anterior sensor clamp 20 includes a lever arm 54, a spring rod 56 and a pivot pin 58. The pivot pin 58 extends from a lower surface 60 of the lever arm 54 and is insertable into a mounting hole 62 (FIGS. 2A and 2B) of the anterior clamp body 24. As shown in FIG. 4, the pivot pin 58 includes a notch 64 that allows a locking flange 66 on the pivot pin distal end 68 to collapse slightly as the flange 66 is pushed through the mounting hole 62. Upon exiting the mounting hole 62, the locking flange 66 resiliently expands over an annular surface 64 (FIG. 2B), thereby locking the release arm 34 onto the clamp body 24. As can be seen in FIG. 2B, the thickness of the clamp body 24 around the mounting hole 62 is minimal and is only as large as necessary to properly secure the release arm 34. Therefore, the mounting hole 62 presents a minimal cylindrical area around the pivot pin 58; and thus, a sterilizing fluid can readily flow in that cylindrical area. As shown in FIGS. 4 and 5, the spring rod 56 has a proximal end 70 rigidly connected to the lever arm 54. With the release arm 34 in the position illustrated in FIG. 5, the spring rod 56 has a quiescent state as illustrated in phantom in FIG. 5. To provide a biasing force on the release arm 34, the spring rod distal end 72 is bent slightly downward as shown in solid in FIG. 5 and placed against a side of a boss or fulcrum 74.

A lever arm outer end 82 is configured to form the release button 36. Depressing the release button 36 causes the release arm 34 to pivot clockwise as viewed in FIG. 5, thereby moving an inner end 86 out of engagement with the clamp slide toothed rack 45 and allowing the clamp slide 28 to be moved with respect to the clamp body 24. Releasing the release button 36 allows the release arm 34 to be rotated counterclockwise as viewed in FIG. 5 by a biasing force applied by the spring rod 56. The release arm inner end 86 has one or more teeth 88 that engage one or more mating teeth 90 of the clamp slide rack 45. Thus, with the release button 36 in its quiescent state, the release arm 34 is engaged with the clamp slide 28 and is effective to lock the clamp slide 28 in a desired position on the clamp body 24.

As shown in FIG. 5, the release arm teeth 88 and the clamp slide teeth 90 have first opposed mating surfaces shown at 91, which are oriented at an acute angle of less than 45 degrees with respect to the clamp slide centerline 32. Thus, if a force is applied against surface 33 of the clamp slide 28, the surfaces 91 of the clamp slide teeth 90 create a horizontal force component that is effective to push the release arm away from the clamp slide 28, thereby allowing the clamp slide 28 to move toward the fixed stop 26. However, the release arm teeth 88 and the clamp slide teeth 90 also have second opposed mating surfaces shown at 93, which are oriented at an acute angle of more than 45 degrees with respect to the clamp slide centerline 32. Thus, if a force is applied against an upper surface 35 of the clamp slide 28, the clamp slide teeth surfaces 93 create a vertical force component that is effective to push the release arm teeth 88 against the clamp slide teeth 90, thereby preventing the clamp slide 28 from moving away from the fixed stop 26. In essence, the shape of the release arm teeth 88 and clamp slide teeth 90 allow the clamp slide 28 to be quickly and easily moved toward the fixed stop 26, while locking the clamp slide 28 at successive incrementally spaced positions as it is moved.

Figure 6:
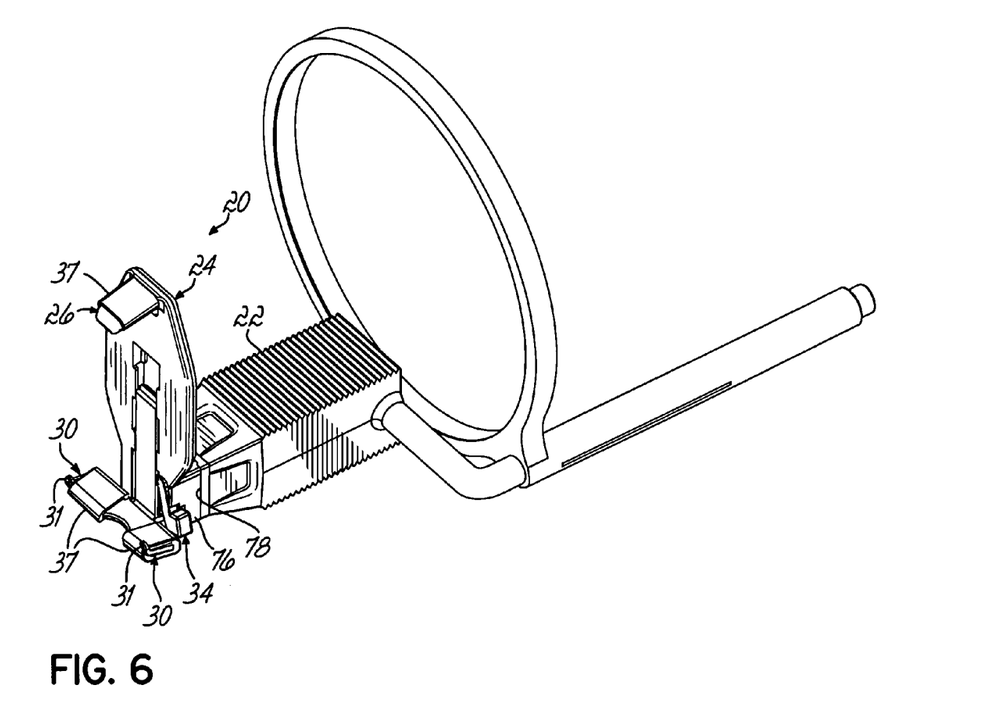
FIG. 6 is a perspective view of the anterior sensor clamp of FIGS. 1A and 1B mounted on an anterior bite plate.

In use, as shown in FIGS. 2A and 2B, the clamp body 24 has a forward extending mounting pin 49 that is inserted into an anterior support or anterior bite plate 22. As the mounting pin 49 is inserted into the bite plate 22, the anterior bite plate 22 has a resilient annular ring (not shown) that pops into an annular groove 51 on the mounting pin 49 in a known manner. Thus, the sensor clamp 20 is secured to the bite plate 22, and the bite plate 22 has opposed lateral walls 94, as shown in FIG. 1A, that maintain the sensor clamp 20 in a desired orientation on the bite plate 22. Referring to FIGS. 1A, 1B and 6, after the sensor clamp is opened by depressing the release button 36 and sliding the resilient arms away from the fixed stop 26, the sensor 38 (shown in phantom) is located between the fixed stop 26 on the clamp body distal end 96 and the resilient arms 30. The sensor 38 is often contained within a hygienic pouch (not shown) in a known manner. Next, the user pushes on a lower surface 33 of the clamp slide 28 at its centerline 32 to secure the flexible arms 30 and sensor 38 against the fixed stop 26. The fixed stop 26 has a downwardly extending projection or claw 27 (FIGS. 2A and 2B), and the resilient arms 30 have upwardly extending respective projections or claws 31. Thus, the projections 27, 31 help hold the sensor 38 in the dental sensor clamp 20.

Continued pressure on the surface 33 causes the resilient arms 30 to flex and apply a resilient clamping force against the fixed stop 26. The release arm 34 automatically locks the clamp slide 28 in place. The protective pads 37 on the fixed stop 26 and resilient arms 30 firmly hold the sensor 38 without damage to the hygienic pouch around the sensor. The resilient clamping forces applied by the resilient arms 30 firmly hold the sensor 38 in the sensor clamp 20 and help to prevent it from moving during an imaging process.

Figure 7:
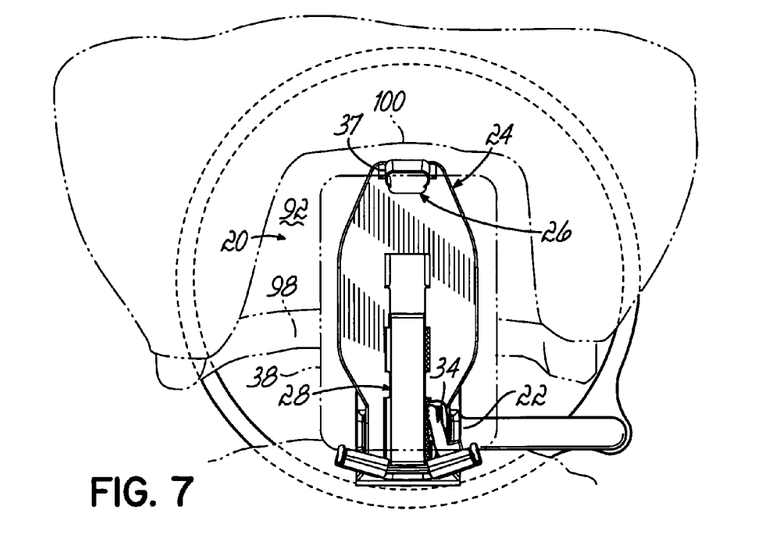
FIG. 7 is an illustration of the anterior sensor clamp of FIGS. 1A and 1B located in an oral cavity in a position to image the anterior teeth, with a view from the posterior to anterior side.

As shown in FIG. 7, the anterior sensor clamp 20 and anterior bite plate 22 are inserted in the patient's oral cavity; and the patient bites down on the bite plate 22. With the anterior sensor clamp 20 described herein, the sensor 38 is always mounted adjacent the apical portions 92 of the patient's teeth 98, thus ensuring that the resulting images will include the apical or root areas of the teeth. It should also be noted that the clamp body proximal end 76 (FIG. 6), the mating rearward end 78 of the anterior bite plate 22 and the external shape of the clamp body 20 are as small as practical to better and more comfortably conform to the oral anatomy of the palate 100 and the arrangement of the anterior teeth 98.

Figure 8A:
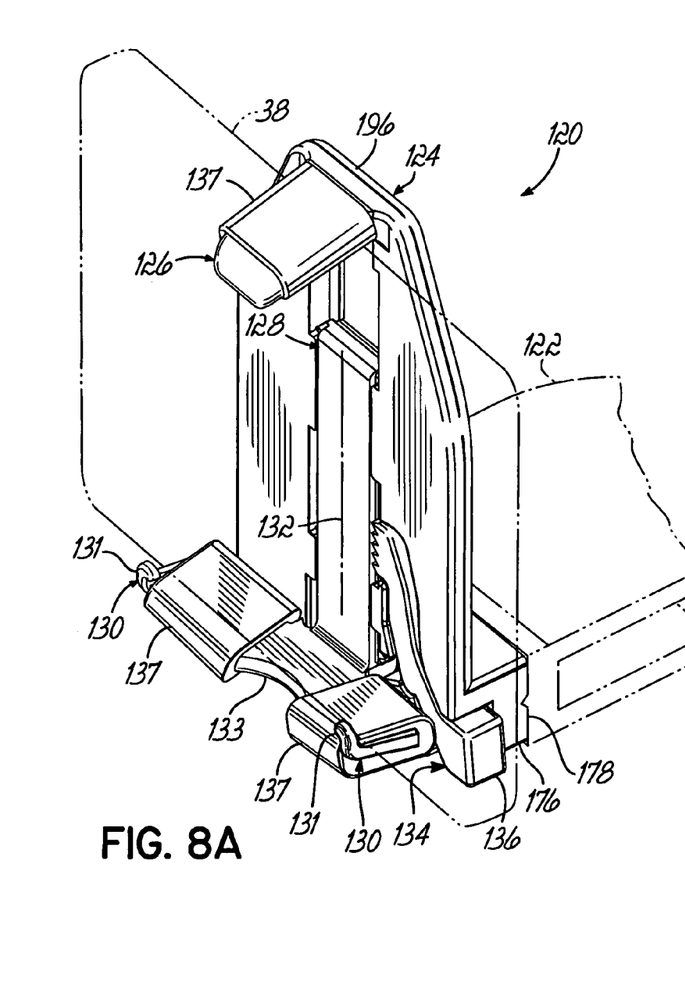
FIGS. 8A and 8B are respective rear and front perspective views of an alternative embodiment of a posterior sensor clamp used to hold a device for imaging posterior teeth in accordance with the principles of the present invention.
Figure 8B:
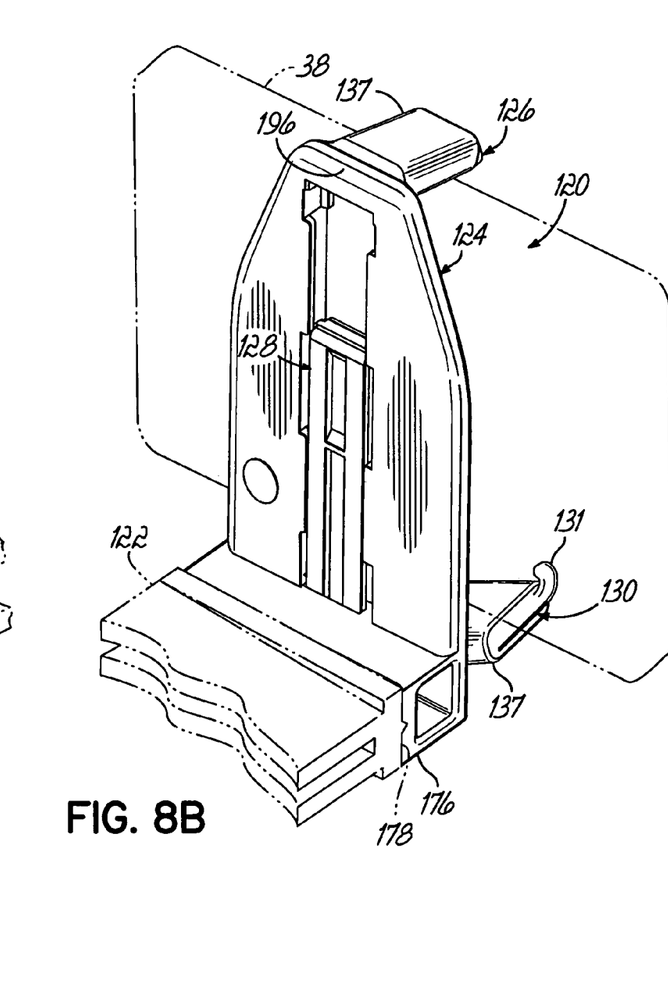

In an alternative embodiment, referring to FIGS. 8A and 8B, a posterior sensor clamp 120 is attachable to a posterior bite plate 122 shown in phantom. With respect to mounting the sensor 38, the posterior sensor clamp 120 is similar in construction and function to the anterior sensor clamp 20 described with respect to FIGS. 1–7. However, as is known, the lateral and rearward location of the posterior teeth as well as the different oral anatomy around the posterior teeth require that the posterior bite plate 122 have a design different from the anterior bite plate 22. Further, obtaining a presentation of the periapical area of the posterior teeth often requires a different sensor or a different orientation of a sensor. Therefore, the base or proximal end 176 of the posterior sensor clamp 120 is wider to match the wider shape of the mating rearward end 178 of the posterior bite plate 122.

The posterior sensor clamp 120 has a posterior clamp body 124 with an upper fixed stop 126. A clamp slide 128 is mounted for sliding movement in a slot 140 of the clamp body 124 and is held in place by pairs of opposed front tabs 146 and rear tabs 148. The clamp slide 128 has a pair of resilient clamping arms 130 that extend in opposite directions from a clamp slide centerline 132. Soft protective pads 137 cover the fixed stop 126 and arms 130. The clamp slide 128 is substantially identical to the clamp slide 28 of FIG. 3. To open the sensor clamp 120, a pivotable posterior release arm 134 is moved out of locking engagement with the clamp slide 128, by pushing a release button 136 formed on an outer end of the release arm 134. With the release button 136 depressed, the clamp slide 128 is movable or slidable with respect to the clamp body 124 in a generally longitudinal direction away from the fixed stop 126. A sensor 38 is then placed between the fixed stop 126 and the resilient arms 130. By pushing on a lower surface 133 of the clamp slide 128 at the centerline 132, the flexible arms 130 and sensor 38 are located against the fixed stop 126. The fixed stop 126 has a downwardly extending projection or claw 127 (FIGS. 9A and 9B), and the resilient arms 130 have upwardly extending respective projections or claws 131. Thus, the projections 127, 131 help hold the sensor 38 in the dental sensor clamp 120.

Continued pressure causes the resilient arms 130 to flex and apply a resilient clamping force against the sensor 38. The release arm 134 automatically locks the clamp slide 128 in place. The pads 137 on the fixed stop 126 and resilient arms 130 firmly hold the sensor 38 without damage to the hygienic pouch (not shown) around the sensor. The sensor 38 is released from the posterior sensor clamp 120 by pushing the release button 136, which unlocks the clamping slide 128. The resilient arms 130 are then free to return to their unflexed state, which causes the clamping slide 128 to quickly move away from the sensor 38; and the sensor clamp 120 "snaps" open.

Figures 9A, 9B:
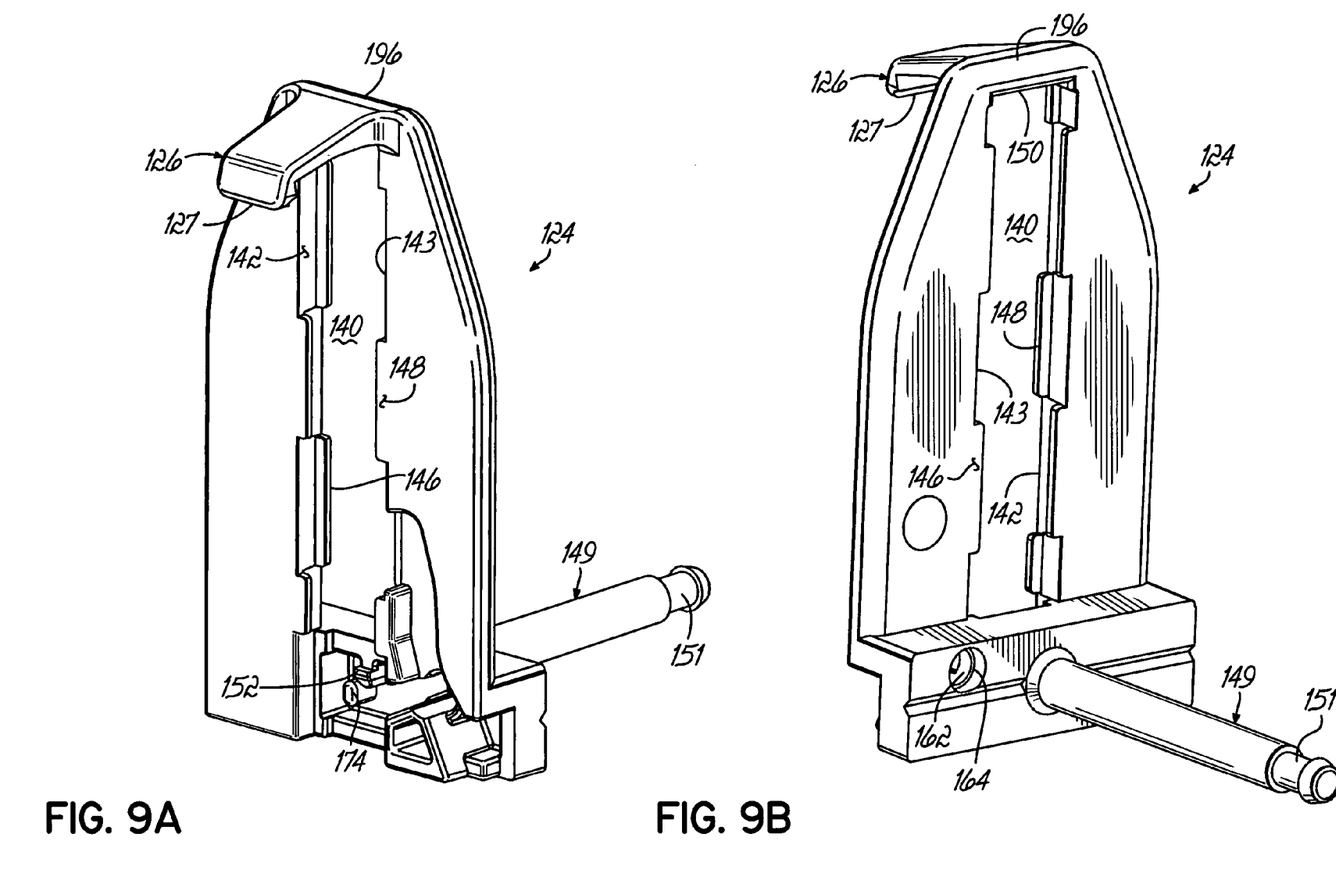
FIGS. 9A and 9B are respective rear and front perspective views of a clamp body used with the posterior sensor clamp of FIGS. 8A and 8B.
Figure 10:
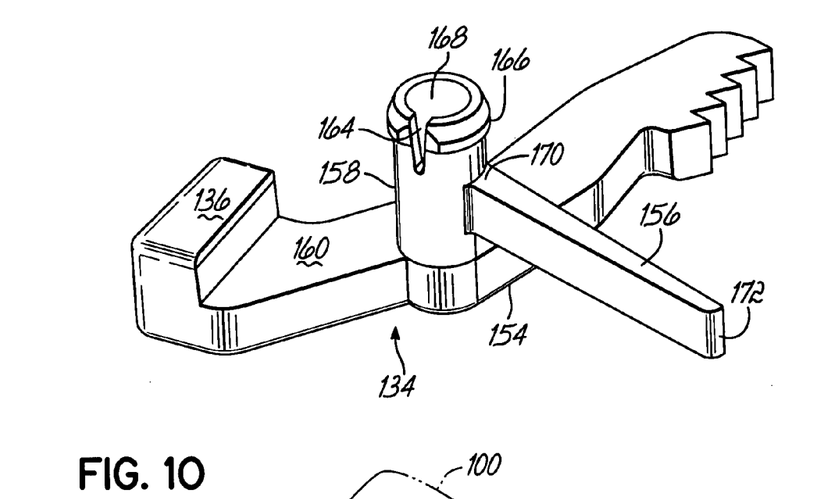
FIG. 10 is a perspective view of a release arm used with the anterior sensor clamp of FIGS. 8A and 8B.

The clamp body 124 of the posterior sensor clamp 120 is shown in detail in FIGS. 9A and 9B and has a centrally located longitudinal slot 140 with opposed side walls 142, 143 and opposed front and rear tabs 146, 148, respectively. The posterior clamp body 124 further has a centrally located fixed clamping stop 126, a mounting pin 149, annular groove 151, slide stop 152 and boss or fulcrum 174. Referring to FIG. 10, the release arm 134 for the posterior sensor clamp 120 includes a lever arm 154 with a release button 136, a spring rod 156 with respective proximal and distal ends 170, 172 and a pivot pin 158 with a notch 164 and locking flange 166 on its distal end 168. Although a different shape from the anterior release arm 34 of FIG. 4, the posterior release arm 134 has a function and operation that is substantially identical to that described with respect to the anterior release arm 34.

Figure 11:
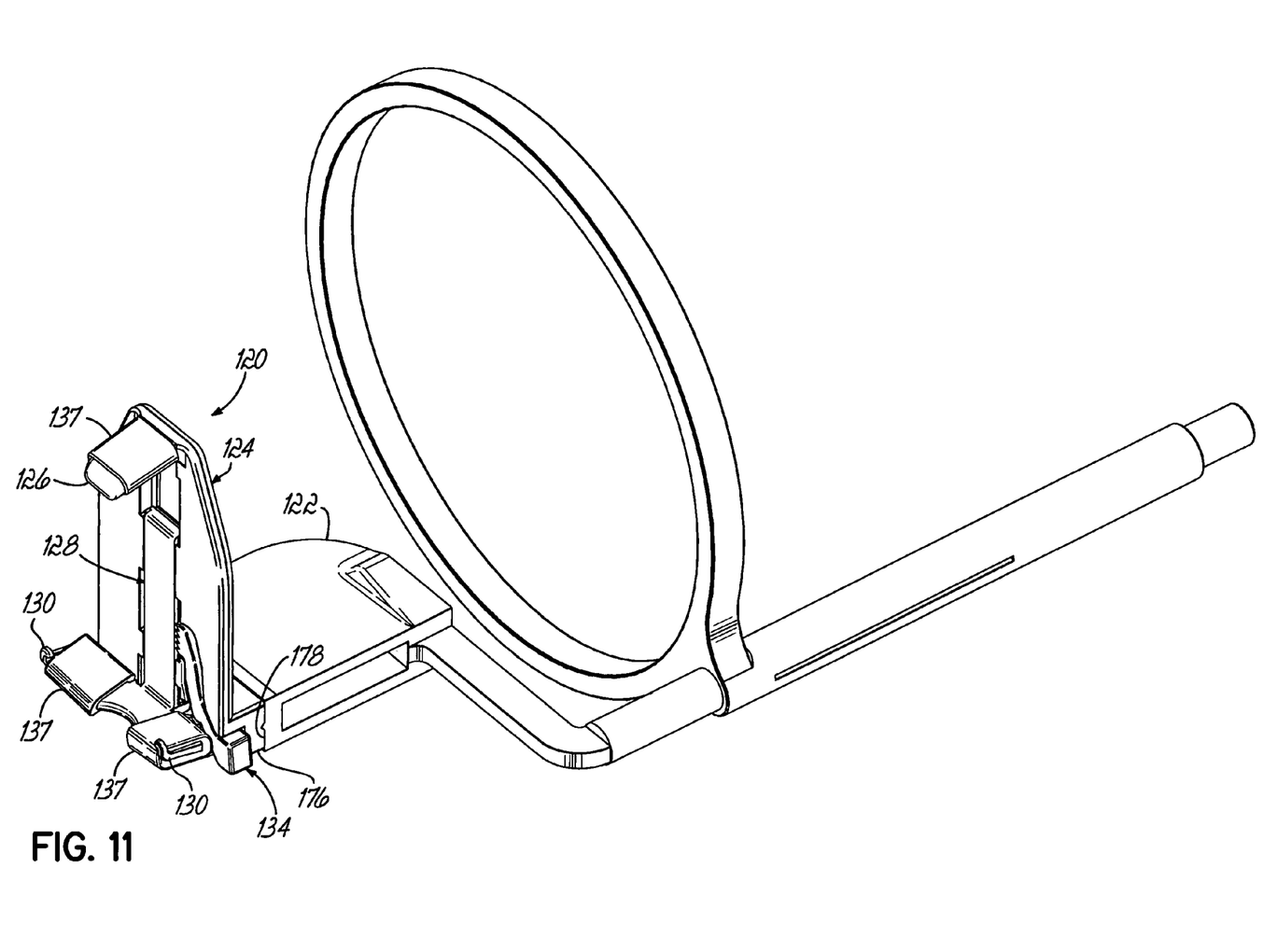
FIG. 11 is a perspective view of the posterior sensor clamp of FIGS. 8A and 8B mounted on a posterior bite plate.
Figure 12A:
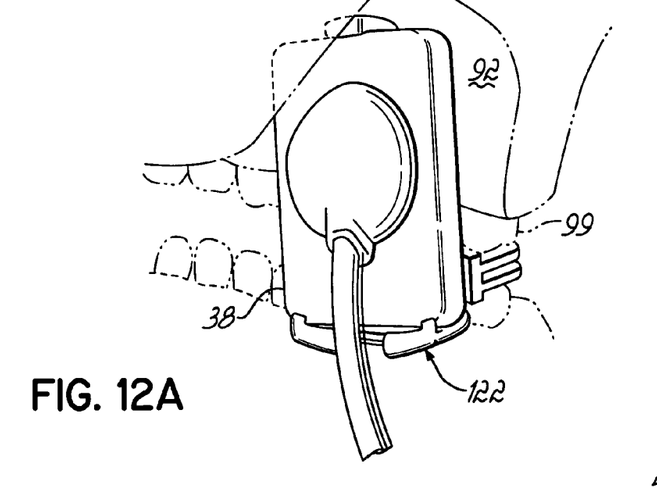
FIGS. 12A and 12B are illustrations of the posterior sensor clamp of FIGS. 8A and 8B located in an oral cavity and holding a sensor in different orientations to image the posterior teeth.
Figure 12B:
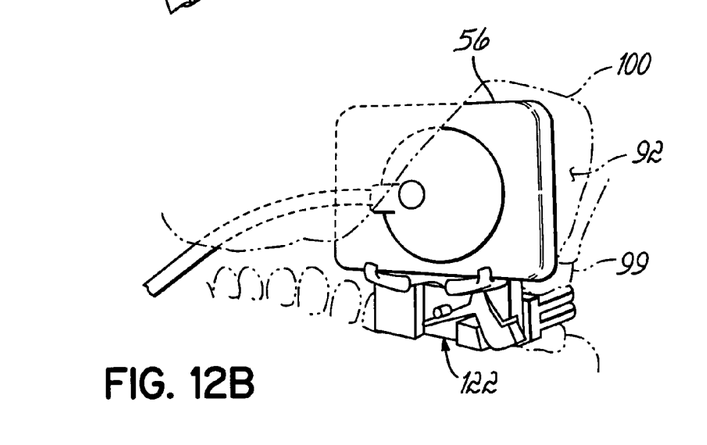

As shown in FIG. 11, the posterior sensor clamp 120 can be mounted on the end of a posterior bite plate 122 and, as shown in FIG. 12A, used with a sensor 38 to provide images of the posterior teeth 99. The posterior sensor clamp 120 has the same advantages as discussed above, that is, ensuring that images will include the apical portions 92 of the posterior teeth 99 and fitting comfortably in the patient's oral cavity. However, as shown in FIG. 12B, the posterior sensor clamp 120 is able to clamp a sensor 38 in different orientations and/or accommodate sensors of different sizes.

The anterior and posterior sensor clamps 20, 120 described with respect to FIGS. 1–12 have numerous advantages. First, the respective anterior and posterior sensor clamps 20, 120 have respective clamp body distal ends 96, 196 that are tapered to be as small as practical and provide respective, small, centrally located, single fixed stops 26, 126. Thus, the anterior and posterior sensor clamps 20, 120 conform with the oral anatomy near the palate 100, with the advantage of fitting more comfortably in the patient's oral cavity. While an exemplary size and shape of the clamp body distal ends 96, 196 are illustrated, other sizes and shapes can be used.

By placing the clamp body distal ends 96, 196 between the palate and the top of the sensor, the sensor clamps 20, 120 have a further advantage of providing the same palatinal condition independent of the sensor being used. Further, the clamp body distal ends 96, 196 can be redesigned to provide other palatinal interfaces that will be consistently achieved independent of the sensor being use. Second, the anterior and posterior sensor clamps 20, 120 locate a sensor against the respective fixed stops 26, 126 and adjacent the apical areas of the teeth. Thus, there is a further advantage in that full presentations of the apical areas of the teeth are reliably obtained and included in images of the periapical area of the teeth.

Third, as shown in FIGS. 1A and 8A, with the anterior and posterior sensor clamps 20, 120, the respective clamping slides 28, 128 and release arms 34, 134 are fully contained within a thickness of respective clamp bodies 24, 124. Thus, all of the areas of respective clamp bodies 24, 124 that overlap an imaging field of the sensor 38 have respective uniform thicknesses. Therefore, the clamp slides 28, 128 and release arms 34, 134 few or no artifacts or shadows in the resulting image. Further, the thicknesses of the respective clamp bodies 24, 124 with the respective clamp slides 28, 128 and release arms 34, 134 are as small as practical, for example, about 2 millimeters. Therefore, the assembly of the clamp bodies 20, 120 and respective clamp slides 28, 128 and release arms 34, 134 produce few or no artifacts or shadows in the resulting image.

Fourth, the anterior and posterior sensor clamps 20 and 120 are active structures having movable parts; but there are no covers or enclosed volumes. The anterior and posterior sensor clamps 20 and 120 have open designs with the advantage that the sensor clamps 20 and 120 can be reliably and effectively sterilized between uses.

Fifth, the anterior and posterior sensor clamps 20 and 120 have a range of adjustability of about 22 mm to 40 millimeters; however, different ranges of adjustability can be readily provided. Thus, there is a further advantage that permits sensors of different sizes to be used.

The clamp bodies 24, 124, clamp slides 28, 128 and release arms 34, 134 can be made of any radiolucent material that can withstand sterilization, multiple uses and provide the functionality described herein. Such materials include but are not limited to polyphenylsulfone, polyetheretherketone and polyetherimide polymers, other amorphous plastics and high performance materials, etc. However, as will be appreciated, the release arms 34, 134 are made of a material that maintains its rigidity after sterilization. Further, the slide clamps 28, 128 and the release arms 34, 134 can be fabricated from different parts or moulded as a single part.

While the present invention has been illustrated by a description of an embodiment, and while such embodiment has been described in considerable detail, there is no intention to restrict, or in any way limit, the scope of the appended claims to such detail. Additional advantages and modifications will readily appear to those skilled in the art. For example, in the described embodiment, the sensor clamp 20 is illustrated as being used with a digital sensor; however, the fixed stop 26, resilient arms 30 and pads 37 can be modified to permit the sensor clamp 20 to be used with other imaging mediums, for example, wired and wireless sensors, imaging plates, film, etc.

In the described embodiment, the release arm 34 is described has having a pivot pin extending from a bottom surface; however, in an alternative embodiment the release arm can be attached to the clamp body using a separate fastener. Further, as described, the release arm 34 has an integral spring rod that is used to provide a biasing force to return the release arm 34 to its rest position. As will be appreciated, in an alternative embodiment, differently shaped and located spring rods as well as separate biasing elements can be used to create a desired biasing force on the release arm.

In the described embodiment, the fixed stop 26, 126 is an integral part of the clamp body 24, 124. In an alternative embodiment, the fixed stop 26, 126 can be made as a separate part that is fastened to the clamp body 24, 124. In further embodiments, the fixed stop can be fastened at different locations along the clamp body centerline 32, 132. In still further embodiments, different fixed stops can be made to have different shapes and sizes, so that they better conform with, and hold, different sensors.

In the described embodiment, oppositely extending resilient arms 30 are mounted on the clamping slide 28 and used to apply a resilient clamping force on the sensor 38. In an alternative embodiment, a single member that is used to apply a resilient clamping force on the sensor 38 can replace the arms 30. As used herein, a "resilient clamping force" means a force that is created by a resiliency that has been designed into the structure, for example, by a deflection of the arms 30, the use of a separate biasing element, such as a spring, etc. or a combination thereof. Thus, minor and imperceptible resilient deflections and deformations that are inherent upon the application of any force onto a body that has not been specifically designed to provide a resilient force are not considered resilient clamping forces within the context of this document.

Therefore, the invention in its broadest aspects is not limited to the specific details shown and described. Consequently, departures may be made from the details described herein without departing from the spirit and scope of the claims which follow.

What is claimed is:

1. A dental sensor clamp for holding a sensor in a mouth of a patient, the dental sensor clamp being supported by a bite plate and the sensor being used to provide images of teeth of the patient, the dental sensor clamp comprising:
   a clamp body comprising
      one end,
      a connector at the one end adapted to be connected to the bite plate,
      an opposite end adapted to be located adjacent an apical area of a tooth, and
      a body portion connecting the one end and the opposite end;
   a fixed stop connected at the opposite end of the clamp body; and
   a clamping slide mounted on, and movable with respect to, the body portion, the clamping slide comprising resilient structure producing a resilient clamping force in a direction toward the fixed stop, the clamping slide being slidable on the body portion toward the fixed stop and adapted to cause the resilient structure to apply the resilient clamping force against the sensor to secure the sensor against the fixed stop.

2. The dental sensor clamp of claim 1 wherein the opposite end of the clamp body and the fixed stop are sized to fit an oral anatomy adjacent an apical area of the tooth.

3. The dental sensor clamp of claim 1 wherein the clamp body comprises a centerline substantially bisecting the fixed stop.

4. The dental sensor clamp of claim 1 wherein the resilient structure comprises resilient arms movable in unison toward the fixed stop.

5. The dental sensor clamp of claim 3 wherein the resilient structure comprises first and second resilient arms extending substantially perpendicular to the centerline.

6. The dental sensor clamp of claim 5 wherein the first and second resilient arms extend in opposite directions.

7. The dental sensor clamp of claim 1 wherein the clamp body comprises a longitudinally extending slot and the clamping slide is located in the slot.

8. The dental sensor clamp of claim 7 wherein the clamping slide comprises a centerline substantially collinear with a centerline of the clamp body.

9. The dental sensor clamp of claim 1 further comprising a locking device mounted on the clamp body and engageable with the clamping slide for securing the member at a desired position with respect to the fixed stop.

10. The dental sensor clamp of claim 9 wherein the locking device comprises:
   a first portion engageable with the clamping slide to secure the clamping slide at a desired position; and
   a second portion adapted to be manually operated to move the locking device to engage and disengage the clamping slide.

11. The dental sensor clamp of claim 10 wherein the first portion and the second portion comprise respectively one end and an opposite second end of the locking device.

12. The dental sensor clamp of claim 11 wherein the clamping slide comprises a plurality of teeth and the one end of the locking device is operable to engage and disengage the plurality of teeth.

13. The dental sensor clamp of claim 12 wherein the locking device comprises a pawl engageable with the plurality of teeth.

14. The dental sensor clamp of claim 12 wherein the locking device comprises a plurality of teeth engageable with the plurality of teeth on the clamping slide.

15. A dental sensor clamp for holding a sensor in a mouth of a patient, the dental sensor clamp being supported by a bite plate and the sensor being used to provide images of teeth of the patient, the dental sensor clamp comprising:
   a clamp body comprising
      a first portion providing one end of the clamp body adapted to be connected to the bite plate,
      a second portion between the one end and the opposite end of the clamp body, the second portion having a substantially uniform thickness over an area of the second portion adapted to overlap an imaging field of the sensor;
   a fixed stop connected at the opposite end of the clamp body; and
   a clamp slide located in the second portion of the clamp body within the thickness, the clamp slide being movable in a first direction toward and away from the fixed stop and adapted to secure and release the sensor against the fixed stop.

16. The dental sensor clamp of claim 15 further comprising a portion of a release arm located in the thickness of the body portion, the release arm being movable to lock and unlock the clamp slide.

17. The dental sensor clamp of claim 15 wherein the substantially uniform thickness is about 2 millimeters.

18. A dental sensor clamp for holding a sensor in a mouth of a patient, the dental sensor clamp being supported by a bite plate and the sensor being used to provide images of teeth of the patient, the dental sensor clamp comprising:
   a clamp body comprising
      one end adapted to be connected to the bite plate,
      an opposite end,
      a slot extending longitudinally in the clamp body,
      tabs extending from opposite walls of the slot,
      an area having a lesser thickness, and
      a mounting hole extending through the area;
   a fixed stop connected at the opposite end of the clamp body;
   a clamp slide located in the slot and between the tabs to be movable in a first direction toward and away from the fixed stop and adapted to secure and release the sensor against the fixed stop; and
   a pivot pin;
   a release arm pivotally mounted to the clamp body by the pivot pin extending through the mounting hole in the clamp body.

19. The dental sensor clamp of claim 18 wherein the clamp body has no portions covering one of the clamp slide and the release arm and therefore does not provide any contained volumes around the one of the clamp slide and the release arm.

20. A method of holding a sensor in a mouth of a patient, the sensor being used to provide images of teeth of the patient, the method comprising:
   providing a clamp body comprising one end connectable to a bite plate, an opposite end, a fixed stop at the opposite end, a body portion connecting the one and opposite ends and having a generally uniform thickness, and a clamping slide being movable on the body portion in a first direction toward and away from the fixed stop to apply a resilient clamping force;

placing a sensor between the fixed stop and the clamping sliding;

sliding the clamping sliding toward the fixed stop and away from the bite plate, the clamping sliding comprising a resilient structure that produces a clamping force toward the fixed stop and against the sensor to secure the sensor against the fixed stop;

inserting the clamp body with the sensor secured thereto in a mouth of a patient and locating the fixed stop adjacent an apical area of a tooth; and fixing the clamp body in the mouth of the patient by having the patient bite the bite plate.

* * * * *

UNITED STATES PATENT AND TRADEMARK OFFICE
CERTIFICATE OF CORRECTION

PATENT NO.       : 7,195,395 B2
APPLICATION NO. : 11/068123
DATED            : March 27, 2007
INVENTOR(S)      : Quarry et al.

It is certified that error appears in the above-identified patent and that said Letters Patent is hereby corrected as shown below:

Column 11, lines 5,6,7,8 CLAIM 20, reads "placing a sensor between the fixed stop and the clamping sliding;
sliding the clamping sliding toward the fixed stop and away from the bite plate, the clamping sliding comprising a resilient structure that produces a" and should read --placing a sensor between the fixed stop and the clamping slide;
sliding the clamping slide toward the fixed stop and away from the bite plate, the clamping slide comprising a resilient structure that produces a--.

Signed and Sealed this

Twentieth Day of November, 2007

JON W. DUDAS
*Director of the United States Patent and Trademark Office*